(12) United States Patent
Ranck et al.

(10) Patent No.: US 8,936,468 B2
(45) Date of Patent: Jan. 20, 2015

(54) TRANSFER COPINGS AND RELATED METHODS FOR TAKING IMPLANT IMPRESSIONS

(76) Inventors: Roger S. Ranck, Ambler, PA (US); Stephen Hogan, Wilmington, DE (US)

( * ) Notice: Subject to any disclaimer, the term of this patent is extended or adjusted under 35 U.S.C. 154(b) by 0 days.

(21) Appl. No.: 13/299,503

(22) Filed: Nov. 18, 2011

(65) Prior Publication Data
US 2012/0135370 A1    May 31, 2012

Related U.S. Application Data

(63) Continuation of application No. 12/355,885, filed on Jan. 19, 2009, now Pat. No. 8,075,313.

(51) Int. Cl.
*A61C 13/12* (2006.01)
*A61C 8/00* (2006.01)

(52) U.S. Cl.
CPC ..................... *A61C 8/0001* (2013.01)
USPC .......................................................... 433/172

(58) Field of Classification Search
CPC ......... A61C 8/0001; A61C 19/04; A61C 8/00
USPC ....................... 433/173–176, 201.1
See application file for complete search history.

(56) References Cited

U.S. PATENT DOCUMENTS

| | | |
|---|---|---|
| 3,793,728 A | 2/1974 | Corbineau |
| 4,281,991 A | 8/1981 | Michl et al. |
| 4,575,340 A | 3/1986 | Lustig |
| 4,622,011 A | 11/1986 | Malek |
| 4,657,510 A | 4/1987 | Gittleman |
| 4,681,542 A | 7/1987 | Baum |
| 4,722,688 A | 2/1988 | Lonca |
| 5,195,891 A | 3/1993 | Sulc |
| 5,334,024 A | 8/1994 | Niznick |
| 5,417,570 A | 5/1995 | Zuest et al. |

(Continued)

FOREIGN PATENT DOCUMENTS

| | | |
|---|---|---|
| EP | 0 438 984 A1 | 7/1991 |
| KR | 20-2002-0035797 | 3/2003 |

(Continued)

OTHER PUBLICATIONS

"Basic Information on the Surgical Procedure," manual, Jan. 2007, 64 pp., Straumann, Basel, Switzerland.

(Continued)

*Primary Examiner* — Cris L Rodriguez
*Assistant Examiner* — Mirayda A Aponte
(74) *Attorney, Agent, or Firm* — Jones Robb PLLC (57) ABSTRACT

A transfer coping configured to take an impression of an implant is disclosed. The transfer coping has an impression material contact portion and an implant mating portion configured to be received within an opening on a coronal portion of the implant. The implant mating portion has at least one support portion and at least one deflection portion. The at least one support portion and the at least one deflection portion are separated from one another by grooves disposed therebetween. The at least one protrusion is disposed on the at least one deflection portion and is configured to engage in a snap-fit manner with a coordinating feature of an implant to maintain engagement of the transfer coping with the implant to take an impression. A method for taking an impression of an implant is also disclosed.

31 Claims, 7 Drawing Sheets

(56) References Cited

U.S. PATENT DOCUMENTS

| | | | |
|---|---|---|---|
| 5,674,073 | A | 10/1997 | Ingber et al. |
| 5,685,715 | A | 11/1997 | Beaty et al. |
| 5,759,036 | A | 6/1998 | Hinds |
| 5,762,500 | A | 6/1998 | Lazarof |
| 5,782,918 | A | 7/1998 | Klardie et al. |
| 5,823,776 | A | 10/1998 | Duerr et al. |
| 5,829,981 | A | 11/1998 | Ziegler |
| 5,904,483 | A | 5/1999 | Wade |
| 5,947,736 | A | 9/1999 | Behrend |
| 6,048,203 | A | 4/2000 | Rosenberg |
| 6,068,478 | A | 5/2000 | Grande et al. |
| 6,068,479 | A | 5/2000 | Kwan |
| 6,083,004 | A | 7/2000 | Misch et al. |
| 6,149,433 | A * | 11/2000 | Ziegler et al. ............... 433/214 |
| 6,155,828 | A | 12/2000 | Lazzara et al. |
| D441,448 | S | 5/2001 | Kumar |
| 6,290,500 | B1 | 9/2001 | Morgan et al. |
| 6,299,447 | B1 | 10/2001 | Zuest et al. |
| 6,332,777 | B1 | 12/2001 | Sutter |
| 6,382,977 | B1 * | 5/2002 | Kumar ............................ 433/214 |
| 6,524,106 | B1 * | 2/2003 | Ziegler .......................... 433/214 |
| 6,540,514 | B1 | 4/2003 | Falk et al. |
| 6,592,370 | B2 | 7/2003 | Morgan |
| 6,644,969 | B2 | 11/2003 | Kumar |
| 6,769,913 | B2 | 8/2004 | Hurson |
| 6,951,460 | B2 | 10/2005 | Halldin et al. |
| 6,981,871 | B2 | 1/2006 | Mullaly et al. |
| 7,014,464 | B2 | 3/2006 | Niznick |
| 7,066,736 | B2 | 6/2006 | Kumar et al. |
| 7,114,952 | B2 | 10/2006 | Morgan |
| 7,137,816 | B2 | 11/2006 | Gervais et al. |
| 7,163,398 | B2 | 1/2007 | Klardie et al. |
| 7,204,692 | B2 | 4/2007 | Klardie et al. |
| 7,207,800 | B1 | 4/2007 | Kwan |
| 7,207,801 | B2 | 4/2007 | Vogt et al. |
| 7,281,924 | B2 | 10/2007 | Ellison |
| 7,300,284 | B2 | 11/2007 | Linder |
| 7,309,231 | B2 | 12/2007 | Engman |
| 7,338,286 | B2 | 3/2008 | Porter et al. |
| 7,632,095 | B2 | 12/2009 | Ostman et al. |
| 8,075,313 | B2 * | 12/2011 | Ranck et al. ............... 433/173 |
| 2002/0177103 | A1 | 11/2002 | Pelak |
| 2003/0082499 | A1 | 5/2003 | Halldin et al. |
| 2003/0114553 | A1 | 6/2003 | Karim et al. |
| 2004/0101806 | A1 | 5/2004 | Kumar et al. |
| 2004/0101807 | A1 | 5/2004 | Porter et al. |
| 2004/0241610 | A1 | 12/2004 | Hurson |
| 2005/0014108 | A1 | 1/2005 | Wohrle et al. |
| 2006/0003290 | A1 | 1/2006 | Niznick |
| 2006/0121416 | A1 | 6/2006 | Engman |
| 2006/0147881 | A1 | 7/2006 | Winter-Moore |
| 2006/0172257 | A1 | 8/2006 | Niznick |
| 2006/0204928 | A1 | 9/2006 | Hurson |
| 2006/0228672 | A1 | 10/2006 | Hurson |
| 2006/0246397 | A1 | 11/2006 | Wolf |
| 2006/0263747 | A1 * | 11/2006 | Hurson ........................ 433/173 |
| 2006/0286508 | A1 | 12/2006 | Bassett et al. |
| 2007/0031103 | A1 | 2/2007 | Tinucci et al. |
| 2007/0031793 | A1 | 2/2007 | Casement et al. |
| 2007/0281278 | A1 | 12/2007 | Jorneus et al. |
| 2007/0281279 | A1 | 12/2007 | Chander |
| 2008/0032263 | A1 | 2/2008 | Bondar |
| 2008/0096168 | A1 | 4/2008 | Schonenberger |
| 2008/0176186 | A1 | 7/2008 | Schaub |
| 2008/0206709 | A1 | 8/2008 | Lannan |
| 2008/0233539 | A1 | 9/2008 | Rossler et al. |
| 2009/0123888 | A1 | 5/2009 | Rosenberg |
| 2009/0123891 | A1 | 5/2009 | Rosenberg |
| 2009/0305195 | A1 | 12/2009 | Jones et al. |
| 2010/0151423 | A1 | 6/2010 | Ranck et al. |
| 2010/0159417 | A1 | 6/2010 | Whipple |
| 2010/0209877 | A1 | 8/2010 | Hogan et al. |

FOREIGN PATENT DOCUMENTS

| | | |
|---|---|---|
| KR | 2003-0030549 | 4/2003 |
| KR | 10-0799368 B1 | 1/2008 |
| WO | WO 03/030768 A1 | 4/2003 |
| WO | WO 2008/093994 A1 | 8/2008 |
| WO | WO 2010/068552 A2 | 6/2010 |
| WO | WO 2010/093737 A2 | 8/2010 |

OTHER PUBLICATIONS

"Basic Information on the Surgical Procedures," manual, Sep. 2007, 79 pp., Straumann, Basel, Switzerland.

"Can You Prevail in the Pursuit of Crestal Bone Preservation?," Certain® Prevail® Implant System, brochure, Rev C Mar. 2008, 8 pp., Biomet 3i™ Palm Beach Gardens, USA.

"Cement-Retained Crowns and Bridges with the Solid Abutment System," catalog, Jan. 2008, 27 pp, Straumann, Basel, Switzerland.

"Immediate Temporary & QuickTemp™ Abutments—Temporary Solutions," catalog, 2007, 4 pp., Nobel Biocare Services AG.

"Restorative Manual," OSSEOTITE® Certain® Implant System and OSSEOTITE® External Hex Connection System, brochure, Rev B dated Nov. 2007, 29 pp., Biomet 3i™, Palm Beach Gardens, USA.

"Simple Solutions Prosthetic Technique Manual," Rev B dated Mar. 2008, 24 pp., BioHorizons USA, Birmingham, USA.

"SPI® Easy—Prosthetic Procedure," brochure, Nov. 2006, 28 pp., Thommen Medical AG, Waldenburg, Switzerland.

"SPI® System—Design Concept," brochure, May 2005, 28 pp., Thommen Medical AG, Waldenburg, Switzerland.

"The Direct Abutment," Astra Tech Implants, brochure, undated, 4 pp., Astra Tech Inc., Lexington, USA.

"XP1 Transmucosal Implant System," [website page online]. Keystone Dental, Inc., [retrieved Mar. 3, 2009], Retrieved from the Internet: <URL: http://www.keystonedental.com/implants/xp1>.

Detailed bibliographic information from KIPRIS website for KR 2003-0030549, original Korean document dated Apr. 18, 2003.

English language abstract of K 2003-0030549, original Korean document dated Apr. 18, 2003.

English language abstract of KR 10-0799368 B1, original Korean document dated Jan. 30, 2008.

English language abstract of KR App. No. 20-2002-0035797, original Korean document dated Mar. 3, 2003.

International Search Report dated Aug. 13, 2010 for International Application No. PCT/US2009/066584.

International Search Report dated Nov. 11, 2010 for International Application No. PCT/US2010/023812.

International Search Report dated Sep. 30, 2010 for International Application No. PCT/US2010/021167.

Lazzara, R. J., DMD, MScD, "Clinical Indications Demonstrating Bone Preservation with the Certain® PREVAIL® Implant," *Clinical Indications*, Certain® PREVAIL® Implant System, brochure, REV A dated Feb. 2007, 12 pp., Biomet 3i™, Palm Beach Gardens, USA.

Östman, P., DDS, "NanoTite™ PREVAIL® Implants: Crestal Bone Preservation in the Aesthetic Zone," *Clinical Perspectives*, NanoTite™ Implant System, brochure, Jul. 2007, 7 pp., vol. 6, Issue 2, Biomet 3i™, Palm Beach Gardens, USA.

Written Opinion of the International Search Authority dated Aug. 13, 2010 for International Application No. PCT/US2009/066584.

Written Opinion of the International Search Authority dated Nov. 11, 2010 for International Application No. PCT/US2010/023812.

Written Opinion of the International Search Authority dated Sep. 30, 2010 for International Application No. PCT/US2010/021167.

Office Action dated Oct. 13, 2010 from U.S. Appl. No. 12/355,885.
Response dated Feb. 14, 2011 from U.S. Appl. No. 12/355,885.
Office Action dated Apr. 20, 2011 from U.S. Appl. No. 12/355,885.
Response dated Jul. 19, 2011 from U.S. Appl. No. 12/355,885.
Office Action dated Jan. 25, 2011 from co-pending U.S. Appl. No. 12/371,563.
Office Response dated May 24, 2011 from co-pending U.S. Appl. No. 12/371,563.
Office Action dated Jul. 20, 2011 from co-pending U.S. Appl. No. 12/371,563.

(56) References Cited

OTHER PUBLICATIONS

Response dated Oct. 20, 2011 from co-pending U.S. Appl. No. 12/371,563.
Office Action dated Nov. 17, 2011 from co-pending U.S. Appl. No. 12/371,563.
Office Action dated Apr. 20, 2011 from co-pending U.S. Appl. No. 12/508,262.
Response dated Jul. 19, 2011 from co-pending U.S. Appl. No. 12/508,262.
Office Action dated Aug. 16, 2011 from co-pending U.S. Appl. No. 12/508,262.
Response dated Dec. 16, 2011 from co-pending U.S. Appl. No. 12/508,262.
Response dated May 17, 2012 from co-pending U.S. Appl. No. 12/371,563.
Response dated Jul. 2, 2012 from co-pending U.S. Appl. No. 12/371,563.
Office Action dated Jul. 11, 2012 from co-pending U.S. Appl. No. 12/371,563.
Response dated Oct. 11, 2012 from co-pending U.S. Appl. No. 12/371,563.
Office Action dated Nov. 6, 2012 from co-pending U.S. Appl. No. 12/371,563.
Office Action dated May 30, 2012 from co-pending U.S. Appl. No. 12/508,262.
Response dated Oct. 29, 2012 from co-pending U.S. Appl. No. 12/508,262.
Office Action dated Nov. 16, 2012 from co-pending U.S. Appl. No. 12/508,262.
Office Action dated May 5, 2014 from co-pending U.S. Appl. No. 13/874,966.

* cited by examiner

TRANSFER COPINGS AND RELATED METHODS FOR TAKING IMPLANT IMPRESSIONS

This application is a continuation of U.S. patent application Ser. No. 12/355,885 (filed on Jan. 19, 2009; now U.S. Pat. No. 8,075,313 B2), the entirety of which is incorporated herein by reference.

TECHNICAL FIELD

The present disclosure relates generally to transfer copings for extra-oral, dental and/or orthopedic implants. The transfer copings may facilitate and/or improve various aspects of taking impressions of such implants.

BACKGROUND

Since the discovery that titanium can fuse to bone, titanium dental implants have represented a growing field of dental reconstruction technology for replacing natural teeth. During implantation, a hole is drilled through the gingiva, the gums surrounding the root of a tooth, and into the jawbone. An implant, which may be made, for example, of titanium or titanium alloy, is then fixed within the hole of the jawbone. Over a period of months, the implant fuses to the jawbone through a process called osseointegration, after which a permanent replacement tooth may be attached to the implant.

In many implant procedures, to form the permanent replacement tooth, a transfer coping (also referred to as an impression coping) is attached to the implant, or an abutment that attaches to the implant, to transfer the position of the implant in the patient to a working model in the dental laboratory. Once the transfer coping is attached to the implant, typically with a separate securing screw, an impression of the patient's dental structure is made using an impression material, such as, for example, polyethyl rubber or polyvinylsiloxane. The impression material, with the transfer coping embedded in the impression material, is then removed and sent to a dental laboratory, where the permanent tooth is fabricated. The position of the implant in the patient is thus identified by the position of the transfer coping within the impression material.

Many conventional transfer copings require a screw to attach the transfer coping to the implant, for example, to internal threading on an implant, while the impression is made. Two methods for making impressions are commonly used: open tray and closed tray techniques. In closed tray techniques, the transfer coping is engaged with the implant and impression material is injected around the coping. The impression is then removed, leaving the transfer coping in place. In open tray techniques, the screw is loosened and then the transfer copings are picked up with the impression material as it is removed. Conventional open and closed tray techniques both use screws to secure the transfer coping to the implant. The use of a screw makes it difficult to locate the implant through the top of the impression tray. Additionally, a conventional transfer coping that requires a screw can't be used if the patient has limitations on opening her mouth when using an open tray technique, thus necessitating retro-fitting the transfer coping back into the impression after it has been removed from the implant using a closed tray technique. This limits the accuracy of the poured stone model and/or increases the chances that the transfer coping is not properly re-oriented into the impression.

Accuracy in the identification of the location is desirable to ensure that the permanent tooth properly fits in the implant and relative to the patient's existing teeth and gumline. Failure to accurately position the permanent tooth could result in patient discomfort and/or failure of the restoration or implant. Thus, there is a long-felt need in the industry for a transfer coping that may accurately and reliably identify the position of dental implants in patients. Moreover, there is a long-felt need for a transfer coping that facilitates the impression process, requiring less manipulation by a dentist or dental technician, and that reduces the chances of having to retro-fit the transfer coping back into the impression material after removal from the implant.

Although various exemplary embodiments of the present teachings may obviate one or more of the above-mentioned problems and/or achieve one or more of the above-mentioned desirable features, it should be understood that some exemplary embodiments may not necessarily obviate one or more of those problems and/or achieve one or more of those desirable features.

SUMMARY

In accordance with various exemplary embodiments, the present teachings contemplate transfer copings that may provide relative accuracy and/or reliability in the identification of dental implant position. Further exemplary embodiments of the present disclosure relate to methods of identifying the position of a dental implant in a patient.

As described herein, various exemplary embodiments of the present teachings include a transfer coping configured to take an impression of an implant, the transfer coping comprising an impression material contact portion and an implant mating portion, wherein the implant mating portion comprises at least one support portion and at least one deflection portion configured to be received within an opening on a coronal portion of an implant, and wherein at least one protrusion is disposed on the at least one deflection portion and is configured to engage in a snap-fit manner with a coordinating feature of an implant.

Various exemplary embodiments of the present teachings further include a method for identifying the position of an dental implant in a patient, comprising, engaging a transfer coping comprising at least one protrusion on a deflection portion and at least one support portion with an implant by snap-fitting the at least one protrusion with the implant, forming an impression around the impression material contact portion with an impression material, and removing the impression with the transfer coping attached.

In the following description, certain aspects and embodiments will become evident. It should be understood that the invention, in its broadest sense, could be practiced without having one or more features of these aspects and embodiments. It should be understood that these aspects and embodiments are merely exemplary and explanatory and are not restrictive of the present teachings or claims.

BRIEF DESCRIPTION OF THE DRAWINGS

The following figures, which are incorporated in and constitute a part of the specification, serve to further illustrate exemplary embodiments of the present teachings. The figures are not, however, intended to be restrictive of the present teachings or claims. In the drawings.

DESCRIPTION OF EXEMPLARY EMBODIMENTS

Reference will now be made to various exemplary embodiments, examples of which are illustrated in the accompanying figures. However, these various exemplary embodiments are not intended to limit the disclosure. To the contrary, the disclosure is intended to cover alternatives, modifications, and equivalents.

The present disclosure contemplates various exemplary embodiments of a transfer coping that can be used to identify the position of an implant in a patient. The transfer coping according to various exemplary embodiments of the present disclosure may attach to an implant, such as a dental implant, without the use of a screw. In at least one embodiment, the transfer coping may be an implant level transfer coping, which may allow the transfer coping to be used without an abutment. The transfer coping according to various exemplary embodiments of the present disclosure may be configured such that an audible sound and/or tactile sensation occurs upon engagement with a dental implant; such an audible sound and/or tactile sensation indicating an accurate engagement of the transfer coping to the implant. The transfer coping of the present disclosure may attach to any implant, such as a dental implant, an extra-oral implant (for example, an eye or ear), or an orthopedic implant.

One exemplary transfer coping of the present disclosure comprises an implant mating portion having a mechanical locking mechanism to engage the transfer coping with the implant.

In at least one exemplary embodiment of the present disclosure, the implant mating portion comprises at least one protrusion that matingly fits to a cooperating feature, for example, an indented feature, such as a groove or undercut, on the implant. The at least one protrusion may comprise various geometric configurations, such as, for example, spherical, semi-spherical, wedge-shaped, triangular, square, rectangular, pyramidal, annular, cube-shaped, etc. For example, the at least one protrusion may comprise a semi-spherical protrusion that fits within a cooperating indentation on the implant.

According to at least one exemplary embodiment of the present disclosure, the implant mating portion of the transfer coping comprises more than one protrusion. For example, the implant mating portion may comprise two, three, or more protrusions. When the implant mating portion comprises more than one protrusion, the protrusions may be spaced evenly or unevenly around the implant mating portion. For example, if the implant mating portion comprises three protrusions, the protrusions may be spaced evenly around the implant mating portion (i.e., at 120° intervals), or the protrusions may be spaced unevenly.

In at least one exemplary embodiment, the implant mating portion attaches to a dental implant without a screw. In at least one embodiment, a screw access channel can be included in the transfer coping to allow a clinician to use a screw to secure a transfer coping onto a dental implant, followed by removal of the screw prior to taking the impression.

In at least one exemplary embodiment, the at least one protrusion on the transfer coping may provide an audible indication and/or tactile sensation to an individual, such as, for example, the dental surgeon or dental technician, attaching the transfer coping to the dental implant. For example, the at least one protrusion may be temporarily deflected by the dental implant as it is engaged with the implant and then produce an audible sound and/or tactile sensation as the at least one protrusion returns to its unbiased (non-deflected) position and "snaps" into place within the cooperating feature on the dental implant. The size and shape of the at least one protrusion and corresponding cooperating securement feature on the implant depends on the desired strength of the fit between the transfer coping and the dental implant, as well as the material comprising the transfer coping and the surrounding structure of the transfer coping. By way of example, the size and shape may be selected so as to provide a sufficiently strong engagement between the transfer coping and the dental implant that permits an impression to be taken without the transfer coping disengaging from the implant during manipulation of the impression material around the transfer coping, yet also permits the transfer coping to be disengaged from the dental implant via exertion of sufficient force by a dental professional when it is desired to remove the transfer coping with the impression material, such as, for example, when two or more implants are divergent.

In at least one exemplary embodiment, the transfer coping may be configured to be engaged and disengaged from a dental implant by movement of the transfer coping in a non-rotative manner, for example, substantially in a longitudinal axial direction relative to the dental implant.

According to at least one exemplary embodiment of the present disclosure, the implant mating portion of the transfer coping may comprise at least one deflection groove to allow at least one or more portions of the implant mating portion to be deflected (e.g., elastically deflected) while pressure is applied to the implant mating portion for positive seating relative to (e.g., engagement with) the dental implant. For example, the implant mating portion may comprise at least one groove or slit-like opening that allows at least one portion of the implant mating portion proximate the at least one groove or opening to be deflected during engagement with the dental implant.

In at least one embodiment of the present disclosure, the implant mating portion may comprise at least two different portions, including at least one deflection portion and at least one support portion. According to at least one embodiment of the present disclosure, the implant mating portion comprises a plurality of alternating deflection portions and support portions.

The at least one deflection portion may comprise the at least one protrusion. The at least one deflection portion according to at least one embodiment of the present disclosure may be flanked by at least one deflection groove to allow the at least one deflection portion to be deflected while pressure is applied to the implant mating portion. When the implant mating portion comprises a plurality of alternating deflection portions and support portions, the implant mating portion comprises localized protrusions. In one exemplary embodiment, the protrusions are localized in that the protrusions are located only on the at least one deflection portion and not on the at least one support portion.

The at least one support portion may allow close mating engagement with the dental implant that may minimize and/or prevent the transfer coping from rotating, pivoting, and/or tilting while engaged with the dental implant. The at least one support portion may be machined to high tolerances to minimize the amount of space between the at least one support portion and a surface of the dental implant with which the at least one support portion mates. The at least one support portion may remain substantially rigid or stationary as the transfer coping engages the dental implant. In various exemplary embodiments, the force required to disengage (e.g., by pulling) the transfer coping from the implant may range from about 0.5 pounds to about 6 pounds, for example, the force may be about 3.5 pounds.

In at least one embodiment of the present disclosure, the implant mating portion may comprise a polygonal shape, such as, for example, a hexagon, multi-jaw coupling or an octagon, or a conical seal design in combination with a polygonal shape. The at least one support portion may comprise at least one side of the polygon. In other embodiments, the at least one support portion may comprise two or more contiguous sides of the polygon or portions thereof. When the at least one support portion comprises two or more contiguous sides or portions of the polygon, contiguous sides or portions thereof may buttress one another and may provide additional support to the transfer coping. In at least one embodiment, the implant mating portion may comprise a curvilinear shape, such as, for example, a circular or oval shape. When the implant mating portion is curvilinear, the at least one support portion may have a curved shape that may resist movement of the transfer coping when it is engaged with the dental implant. According to at least one embodiment of the present invention, the implant mating portion may comprise a configuration designed to mate to an indexed or non-indexed dental implant.

The transfer coping according to at least one exemplary embodiment of the present disclosure may further comprise at least one additional mechanical binding aid to secure the transfer coping to the dental implant. The at least one additional mechanical binding aid may be chosen from, for example, a friction fit, a roughened surface, protrusions, grooves, indentations, etc. For example, the transfer coping may comprise a friction fit taper on an internal coronal aspect of the transfer coping. The friction fit taper may stabilize the transfer coping to improve the accuracy of the identification of the position of the implant when taking the impression.

Transfer copings in accordance with various exemplary embodiments of the present disclosure also may comprise an impression material contact portion. Once the transfer coping is attached to the dental implant, an impression can be taken, for example with a closed dental tray, with which those having ordinary skill in the art are familiar. The impression material surrounds the impression material contact portion of the transfer coping and securely attaches the impression to the transfer coping once the impression material has cured.

In at least one exemplary embodiment of the present disclosure, the impression material contact portion may comprise at least one indentation, flange, and/or other feature to provide an increased contact surface area between the impression material and the impression material contact portion. The at least one indentation, flange, and/or other feature may comprise various forms or textures (e.g., surface textures) to improve contact between the impression material and the transfer coping, such as, for example, grooves, ridges, dimples, etc. The at least one indentation, flange, or other feature may have an even or uneven surface, such as surface roughening or serrations.

The impression material contact portion of the transfer coping may be sized based on the coronal dimension of the implant (i.e., the diameter of the top of the implant) and/or the space between the implant and opposing dentition, and as such, would be readily determined by one skilled in the art depending on the needs of the patient.

The transfer coping according to various exemplary embodiments of the present disclosure may comprise a material chosen from metal, ceramic, plastic, and/or combinations thereof. In at least one exemplary embodiment, the transfer coping comprises a material chosen from stainless steel, titanium, and titanium alloys. In at least one exemplary embodiment of the present disclosure, the transfer coping comprises a material that is radiopaque. A radiopaque transfer coping may be observable using an X-ray, which may aid in locating the implant in the patient's mouth and the position of the transfer coping in the impression, and/or aid in the confirmation of the engagement between the dental implant and the transfer coping.

The present disclosure also relates to a method for identifying the position of an implant in a patient.

In at least one exemplary embodiment of the present disclosure, the method of identifying the position of an implant, such as a dental implant, in a patient comprises providing a transfer coping comprising an implant mating portion and an impression material contact portion. The method may include moving the transfer coping in a direction generally along a longitudinal axis of and toward the dental implant and matingly fitting at least one protrusion of the implant mating portion with a cooperating feature, such as, for example, an indentation, on a dental implant to engage the transfer coping with the dental implant. Once the transfer coping has been attached to the dental implant, an impression material is inserted around the impression material contact portion of the transfer coping and the surrounding area, and the impression material is cured. After the impression material has cured, the impression material, with the transfer coping attached or embedded therein, is removed. The impression material and the transfer coping may be removed by pulling the transfer coping off the dental implant, e.g., by moving the transfer coping in a direction generally along the longitudinal axis of the dental implant and away from the dental implant. The impression may then be sent to a dental laboratory where the permanent tooth is fabricated. While the above exemplary embodiment is described with reference to a dental implant, the method presently disclosed may be used for other implants, such as extra-oral or orthopedic implants.

Figure 1:
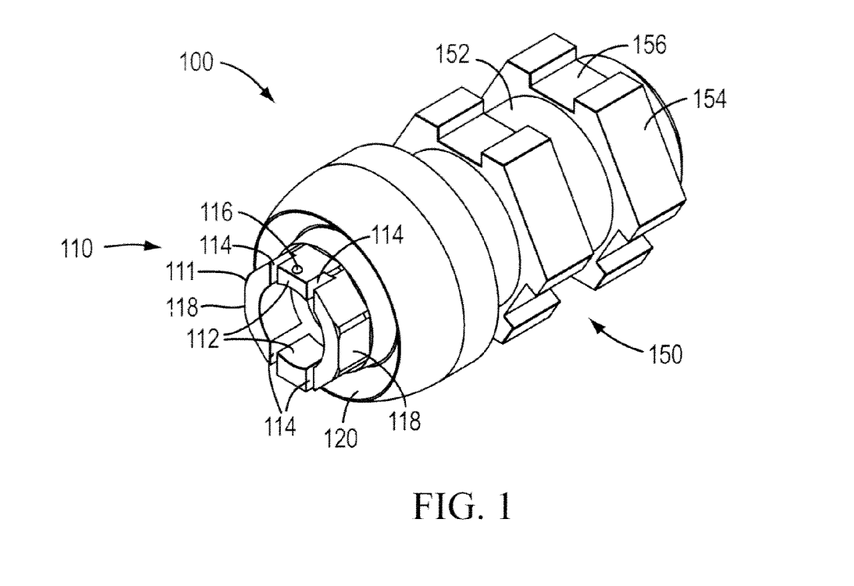
FIG. 1 is a perspective view of a transfer coping according to an exemplary embodiment of the present disclosure.

With reference now to FIGS. 1-4, various views of an exemplary embodiment of a transfer coping in accordance with the present teachings is illustrated. FIG. 1 shows a perspective view of a transfer coping according to an exemplary embodiment of the present disclosure. In FIG. 1, the transfer coping 100 comprises an implant mating portion 110 and an impression material contact portion 150.

Figure 2:
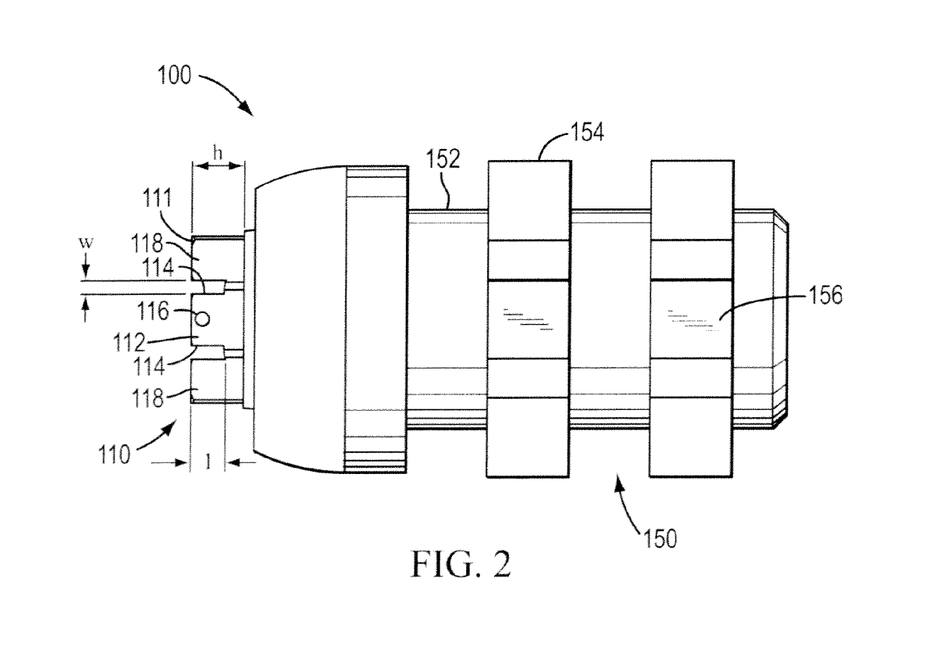
FIG. 2 is a side view of the transfer coping of FIG. 1.

The impression material contact portion 150 comprises a generally cylindrical portion 152 having a plurality of flanges 154 situated around portion 152. Flanges 154 shown in FIGS. 1-4 are in the form of annular hexagons surrounding cylindrical portion 152. Flanges 154 comprise a plurality of serrations 156 that may further increase the contact between the transfer coping and the impression material. A side view of transfer coping 100 is shown in FIG. 2. Those having ordinary skill in the art would understand that the configuration of the flanges 154 shown in the exemplary embodiment of FIGS. 1-4 is exemplary only and other configurations may be utilized without departing from the scope of the present disclosure. The impression material contact portion 150 may include other features, including surface texturing, roughening and/or other surface features, and/or other configurations such as are described above to enhance contact and retention in an impression material. Those having ordinary skill in the art are familiar with such configurations and/or modifications of impression material contact portions of dental transfer copings.

In the exemplary embodiment shown, implant mating portion 110 includes a friction fit taper portion 120 and a generally octagonally-shaped portion 111. The octagonal portion 111 is configured to fit within a coronal opening of a dental implant, such as, for example, in coronal opening 510 of the dental implant 500 illustrated in the exemplary dental implant embodiment of FIGS. 5 and 6. One or more protrusions 116 may be disposed on an external surface of one or more of the sides 112 of the octagonal portion 111 (e.g., on two opposite sides 112 in the exemplary embodiment of FIGS. 1-4).

Figure 5:
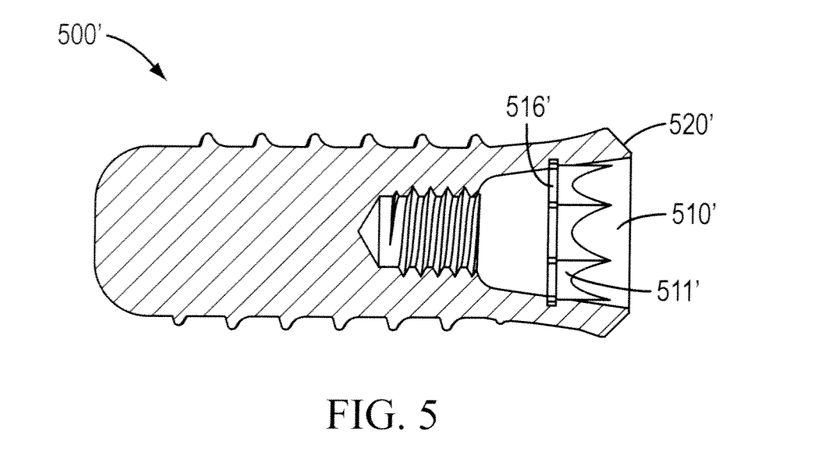
FIG. 5 is a cross-sectional view of an exemplary embodiment of a dental implant with which transfer copings according to various exemplary embodiments are configured to engage.
Figure 6:
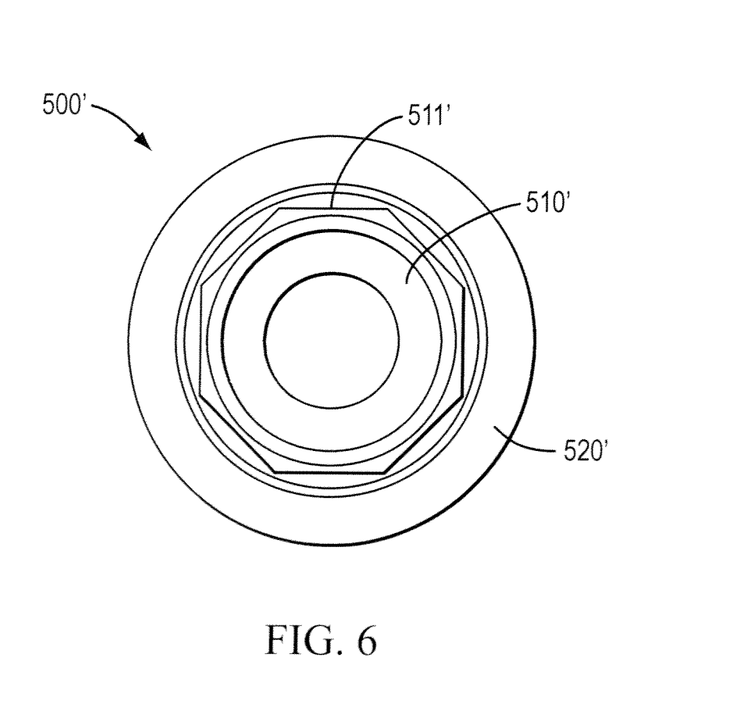
FIG. 6 is an end view of the dental implant of FIG. 5.

The one or more protrusions 116 are configured to matingly fit to a cooperating feature of a dental implant, such as, for example, a dental implant 500' as shown in FIGS. 5 and 6. For example, protrusions 116 may be generally semi-spherical in shape (e.g., having a radius of about 0.006 inch) and may be configured to fit, for example, via a snap-fit, into cooperating features (e.g., indented or grooved region formed by an undercut region 516') of dental implant 500', which may have an angle of indentation ranging from about 20° to about 40°. When implant mating portion 110 of transfer coping 100 is engaged with dental implant 500', protrusions 116 may provide an audible sound and/or tactile sensation that informs the individual engaging the transfer coping 100 to the dental implant 500' that the transfer coping 100 has been seated and engaged properly.

As shown in FIGS. 5 and 6, the implant 500' may include a coronal opening 510' at a coronal portion 520' thereof configured to receive a transfer coping (e.g., the octagonal portion 111 of the transfer coping 100) and/or additional replacement tooth components. The coronal opening 510' in accordance with various exemplary embodiments may include an octagonal inner surface 511', as shown best in the cross-section of FIG. 6. The octagonal portion 111 of the transfer coping 100 may be correspondingly configured, as described above, to be received by and mate with the octagonal inner surface 511' of the implant 500'. In accordance with various exemplary embodiments, the implant mating portion 110 may be configured to engage with the coronal portion of a variety of conventional implants, including, for example, various implants made by Straumann of Switzerland. Non-limiting examples of other dental implants that may be engaged with the transfer coping of the present disclosure may include any dental implant with an indented feature, such as a groove or ledge, configured to permit a mating fit (e.g., snap-fit) with a cooperating protrusion, either horizontal or vertical, such as the Zimmer SwissPlus and Keystone Dental Stage-1 dental implants, and the Aeton single-stage dental implant comprising a 4.1 mm, 4.8 mm or 6.5 mm neck and an internal Morse taper-like/conical seal design (e.g., an 8° Morse taper-like) with an octagonal opening, as shown in FIG. 6. Conventional dental implants generally comprise a threaded exterior portion that attaches to the jawbone of a patient and interior threads designed to receive restorations or other fixtures. Those of ordinary skill in the art would be familiar with the various conventional dental implant configurations and features useful with the transfer copings of the present teachings.

Figure 9:
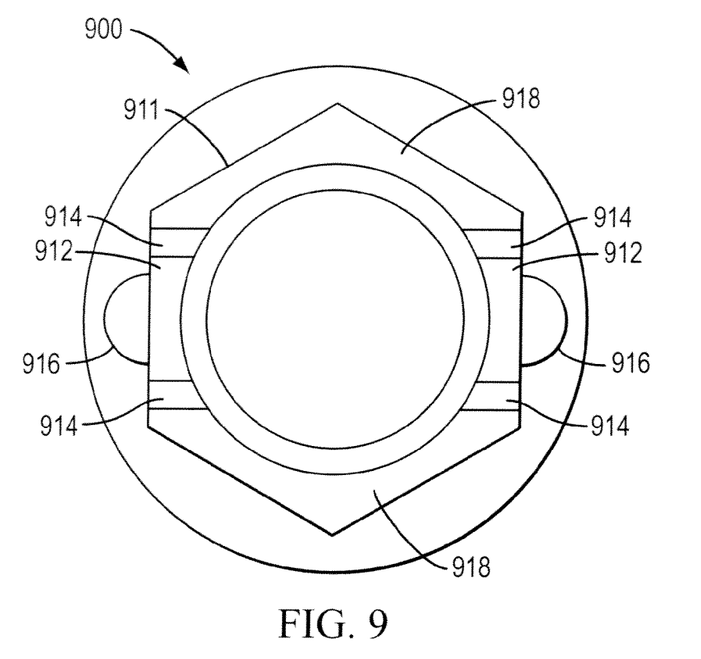
FIG. 9 is an end view of a transfer coping according to yet another exemplary embodiment of the present disclosure.
Figure 10:
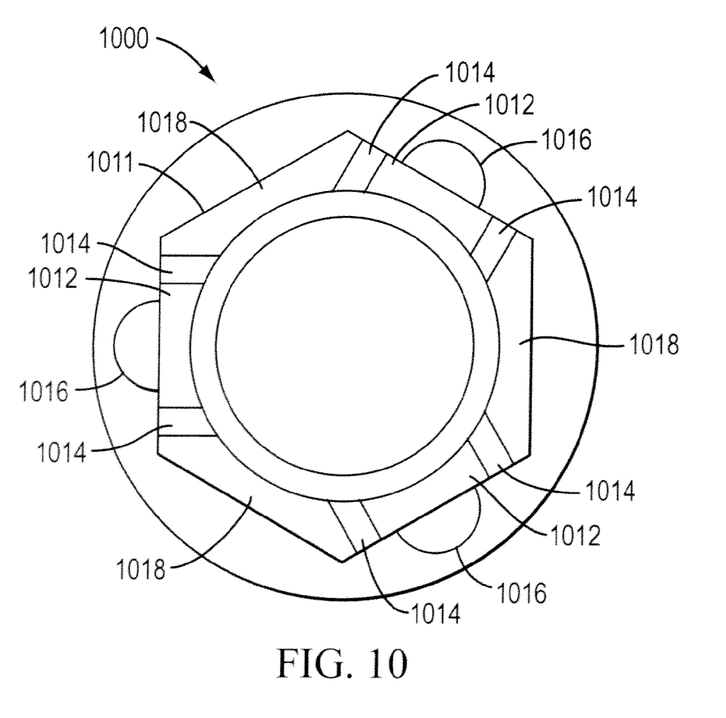
FIG. 10 is an end view of a transfer coping according to another exemplary embodiment of the present disclosure.

Those having ordinary skill in the art will appreciate that the portion of the transfer coping that carries the protrusions may have shapes other than octagonal and may be configured so as to engage with implants having openings that likewise have shapes other than octagonal. For example, any polygonal shape may be selected so as to provide an anti-rotational engagement of the transfer coping with the implant, although other non-polygonal shapes also are within the scope of the present teachings. For example, other exemplary implant mating portion geometries are shown in FIGS. 9 and 10, which will be described in further detail below.

Figure 4:
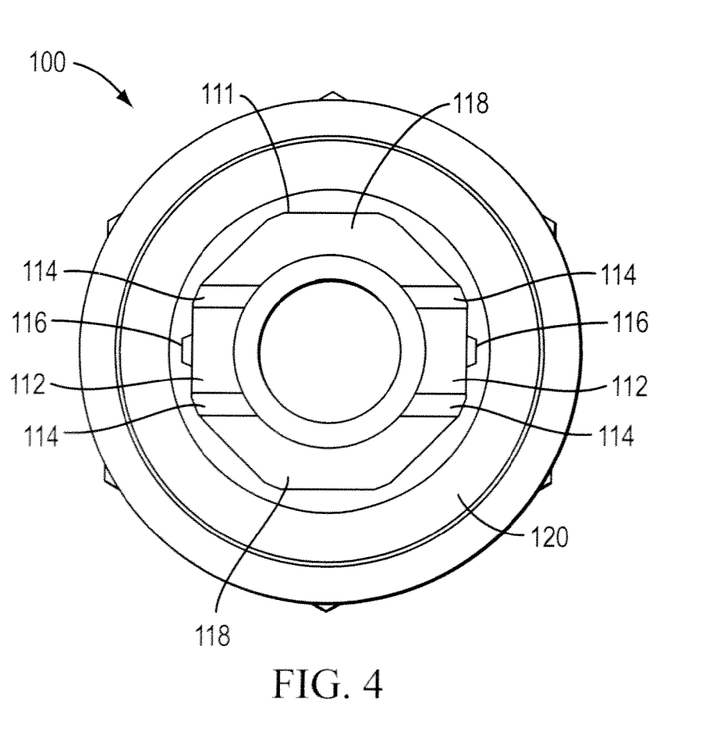
FIG. 4 is an end view of the transfer coping of FIG. 1.

As shown best in FIGS. 2 and 4, the octagonal portion 111 may have a height, h, ranging from about 0.035 in. to about 0.045 in., for example, the height may be about 0.039 in. A plurality of deflection grooves 114 may be provided on at least some sides of the octagonally-shaped portion 111 to define deflection portions 112. For example, two deflection grooves 114 may be provided on either side of deflection portions 112 so as to define the deflection portions 112. The deflection grooves 114 permit the deflection portions 112 to move (e.g., elastically deflect) slightly in a radial direction. For example, the portions 112 may move slightly radially inwardly when a force having a radially inwardly directed component is applied and then may return to their unbiased, non-deflected position when the radially inward force is removed. In this way, as the transfer coping 100 is being engaged with an implant, the coronal portion of the implant may exert a radially inward force on the portions 112 causing them to deflect slightly radially inwardly. Once the protrusions 116 reach the cooperating feature (e.g., region 516' in FIG. 5) of the implant, the portions 112 may return to their non-deflected position, with the return back to that position and the protrusions 116 creating a snap-fit engagement that provides an audible and/or tactile sensation to indicate proper engagement with the implant. This elastic radial deflection may occur even when the transfer coping 100 is made of a metal or metal alloy material. By disposing the protrusions 116 on the deflection portions 112, the snap-fit engagement may occur between the implant mating portion 110 and the corresponding cooperating indentation region on the dental implant 500'. When the transfer coping 100 is disengaged from the dental implant 500', the protrusions on the deflection portions 112 elastically deflect in the same manner as during engagement.

In at least one embodiment, a snap-fit engagement may be possible by positioning and sizing the protrusions 116 in a way that they may contact the walls of inner surface 511' as the implant mating portion 110 enters the coronal opening 510' and elastically deflect the deflection portions 112. Once the protrusions 116 reach the undercut regions, the deflection portions 112 may spring back to their undeflected state. An audible sound may be produced when the deflection portions 112 revert to their undeflected state, which may provide an indication that the transfer coping 100 has been properly seated in the implant 500'.

Deflection grooves 114 may be sized and shaped to permit the deflection portions to deflect inwardly and outwardly (e.g., radially inwardly and outwardly) relative to remaining portions of the implant mating portion 110 as the implant mating portion 110 engages the dental implant 500'. The deflection grooves 114 may extend partially (as shown in FIGS. 1-4) or entirely along the height, h, of the octagonally-shaped portion 111. By way of example only, deflection grooves 114 shown in FIGS. 1 and 2 have a width, w, ranging from about 0.008 in. to about 0.012 in., for example, about 0.010 in., and a length, I, ranging from about 0.035 in. to about 0.040 in., for example, about 0.038 in. The deflection grooves 114 may be formed through the thickness of the octagonal portion 111.

With reference to FIGS. 4, 9 and 10, which show end views of exemplary embodiments of transfer copings viewed from the implant mating portion of the transfer copings, differing configurations of implant mating portions, deflection grooves, and deflection and support portions are depicted in accordance with the present disclosure. The arrangements of deflection grooves and protrusions, as well as the geometry of the implant mating portion, shown in FIGS. 4, 9, and 10 are non-limiting, exemplary embodiments according to the present disclosure. One of ordinary skill in the art would appreciate that the present disclosure covers other arrangements of the deflection grooves, protrusions, and implant mating portion.

FIG. 4, described above, is an example of an implant mating portion having an octagonal portion 111 comprising two deflection portions 112 and two support portions 118. Each deflection portion 112 comprises a protrusion 116.

FIG. 9 shows a transfer coping 900 having an implant mating portion that includes a hexagonal portion 911 rather than the octagonal portion 111 of the exemplary embodiment of FIGS. 1-4. The hexagonal portion 911 comprises two deflection portions 912 situated substantially opposite to one another and two support portions 918 also situated substantially opposite to one another and between the two deflection portions 912. Deflection portions 912 are flanked by a plurality of deflection grooves 914 and comprise localized protrusions 916. Each of the support portions 918 comprise two contiguous sides of the hexagonal portion 911. Thus, each side of support portions 918 is buttressed by one other side if the hexagonal portion 911.

FIG. 10 shows a transfer coping 1000 having an implant portion that includes a hexagonal portion 1011 comprising three deflection portions 1012 and three support portions 1018. Deflection portions 1012 are flanked by a plurality of deflection grooves 1014 and comprise three protrusions 1016. Each of the support portions 1018 is formed by one side of the hexagonal portion 1011 that is contiguous on either side with at least a portion of a side of the hexagonal portion 1011.

Figure 3:
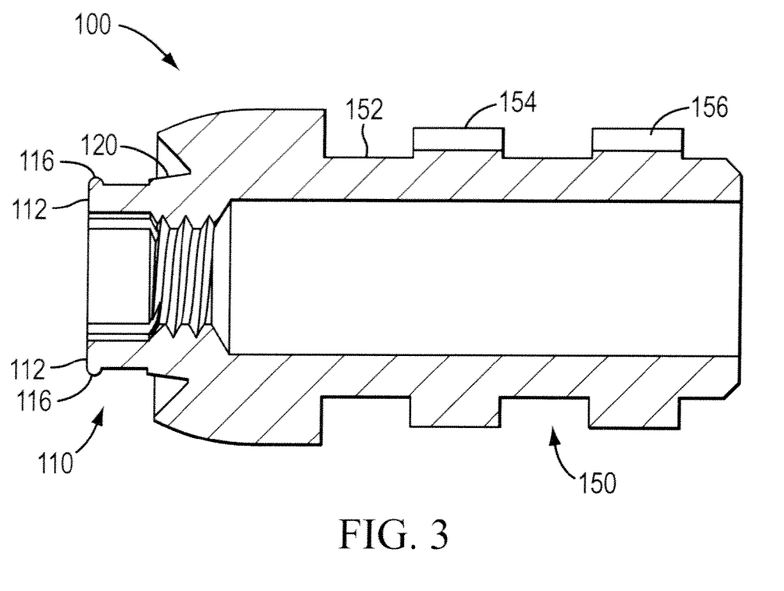
FIG. 3 is a cross-sectional view of the transfer coping of FIG. 1.
Figure 11:
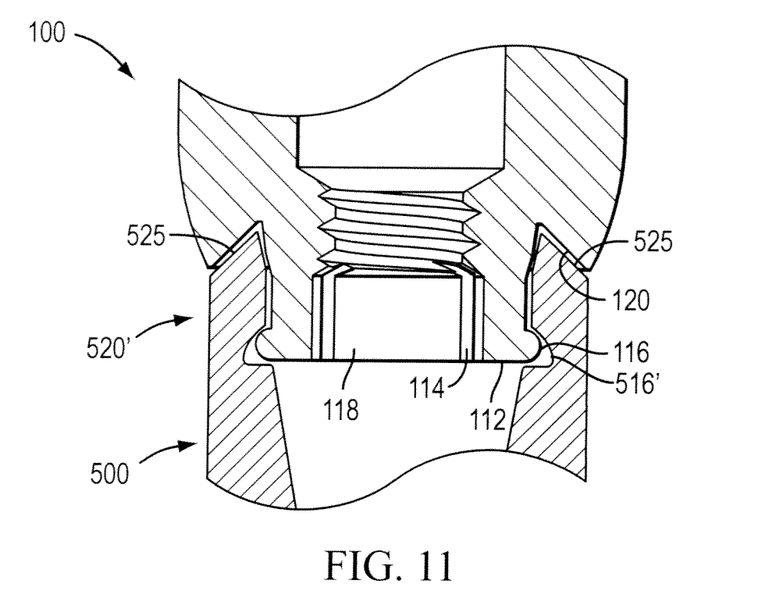
FIG. 11 is a partial cross-sectional view of a transfer coping engaged with an implant according to an exemplary embodiment of the present disclosure.
Figure 12:
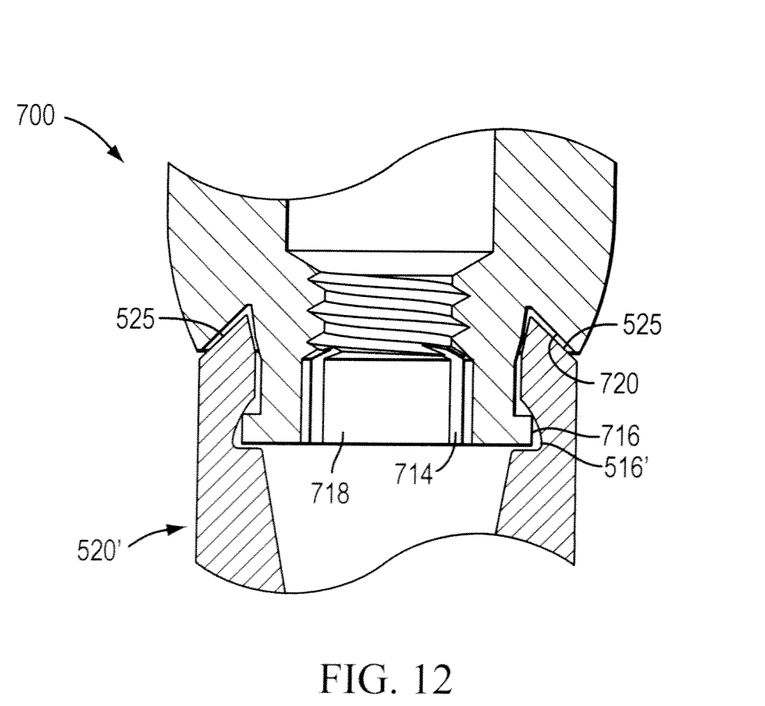
FIG. 12 is a partial cross-sectional view of a transfer coping engaged with an implant according to another exemplary embodiment of the present disclosure.

As best shown in the cross-sectional view of FIG. 3 and end view of FIG. 4, the implant portion 110 of transfer coping 100 also comprises a friction fit taper 120 proximate the coronal end of the octagonal portion 111 that is configured to mate with a coronal portion of a dental implant, such as the coronal portion 520' of the dental implant 500' (such engagement being best shown in the exemplary embodiments of FIGS. 11 and 12). Friction fit taper 120 may provide an enhanced fit with the dental implant by engaging the coronal portion 520' of the implant 500'. Friction fit taper 120 may have various taper angles configured to engage with the various taper angles of dental implants, at least some of which are readily known to those having ordinary skill in the art. For example, the taper angle may range from about 3° to about 20°, such as, for example, an 8° taper angle. The taper angle may be Morse taper-like, for example. Friction fit taper 120 is sized to engage in a friction fit manner with coronal portion 520' of dental implant 500', thereby providing an additional securing mechanism when engaging the transfer coping 100 and the dental implant 500'. Those having ordinary skill in the art are familiar with various friction fit taper structures on transfer and other copings that engage with shoulders of correspondingly tapered dental implants. In at least one exemplary embodiment of the present disclosure, the transfer coping does not comprise a friction fit taper on the implant mating portion, i.e., that portion is parallel to the longitudinal axis rather than tapered.

Figure 7:
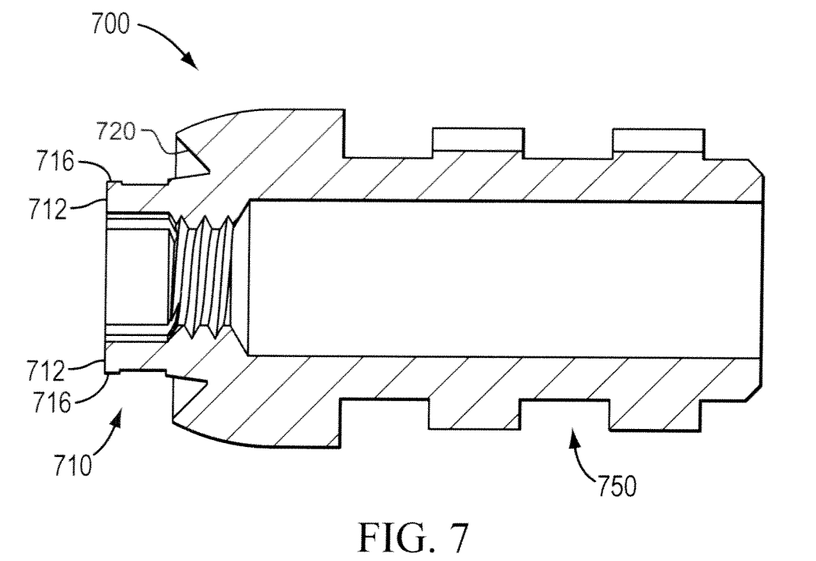
FIG. 7 is cross-sectional view of a transfer coping according to another exemplary embodiment of the present disclosure.
Figure 8:
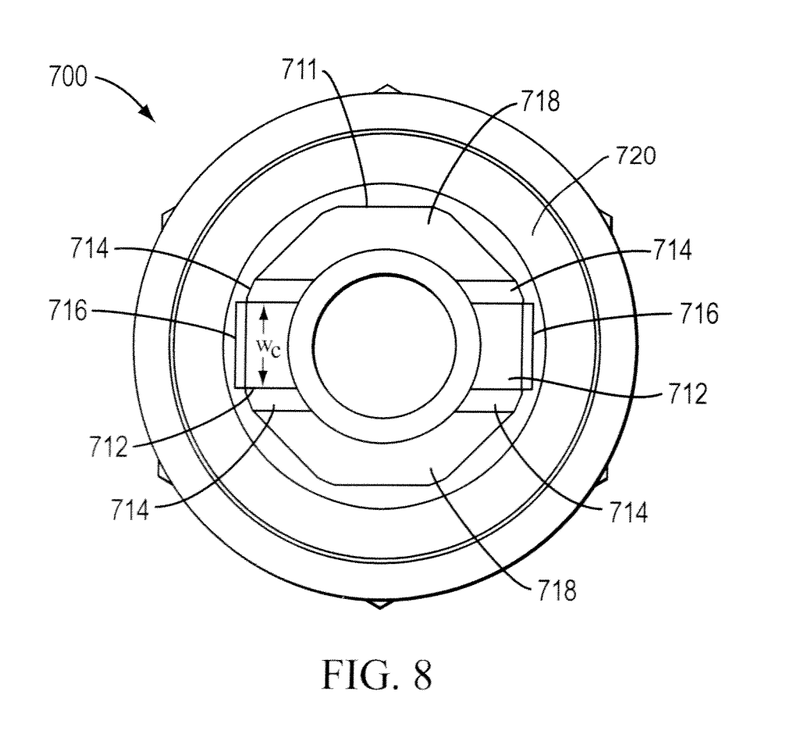
FIG. 8 is an end view of the transfer coping of FIG. 7.

The protrusions of the implant mating portion may comprise a variety of configurations. Transfer coping 100, as shown in FIGS. 1-4, comprises semi-spherical protrusions 116. FIGS. 7 and 8 show another exemplary embodiment of the present disclosure having protrusions of a differing shape than the exemplary embodiment of FIGS. 1-4. In particular, FIG. 7 is a cross-sectional view of the transfer coping 700 similar to the cross-sectional view of FIG. 3, and FIG. 8 is an end view of the transfer coping 700 similar to the end view of FIG. 4. As shown in FIGS. 7 and 8, transfer coping 700 comprises an implant mating portion 710 and an impression material contact portion 750. Implant mating portion 710 comprises an octagonal portion 711 that comprises a plurality of deflection portions 712 flanked by deflection grooves 714 and having rectangular protrusions 716. The width of rectangular protrusions 716 may range from about 0.008 in. to about 0.012 in., for example, the width may be about 0.010 in. The length of rectangular protrusions 716 may range from about 0.025 in. to about 0.030 in., for example, the length may be about 0.028 in. Rectangular protrusions 716 may have a surface area of about 0.0003 in.$^2$. Other dimensions of rectangular protrusions 716 are also contemplated by the present disclosure and would be recognized by one of ordinary skill in the art to depend on the size of the dental implant, configuration of the cooperating feature (e.g., size and shape of the groove or undercut) of the dental implant, and other factors. Implant mating portion 710 further comprises a plurality of support portions 718. As can be seen in the end view of FIG. 8, protrusions 716 extend partially across the width, $w_c$, of deflection portions 712 between the deflection grooves 614. In at least one exemplary embodiment, the protrusions 716 may extend at least about 50% across the width $w_c$ of deflection portions 712, such as at least about 75% or at least about 90%. According to at least one exemplary embodiment, the protrusions 716 may extend at least about 95%, at least about 97%, or at least about 99% across the width $w_c$ of deflection portions 712. In an alternative configuration, the rectangular protrusions 716 may extend across the entire width, $w_c$, of the deflection portions 712.

In at least one exemplary embodiment of the present disclosure, protrusions 716 may cover about 20% to about 30% of the area of deflection portions 712. One of ordinary skill in the art would recognize that the length of the protrusions are chosen based on the desired level of engagement between the transfer coping and the dental implant (e.g., the pull-off force required to disengage the transfer coping from the dental implant), and as such, the dimensions of the protrusions with respect to the deflection portions depend on the size of the transfer coping and the dental implant, the geometry of the protrusions, the geometry of the complimentary features of the dental implant, as well as the materials used to fabricate the transfer coping and the dental implant.

Figure 13A:
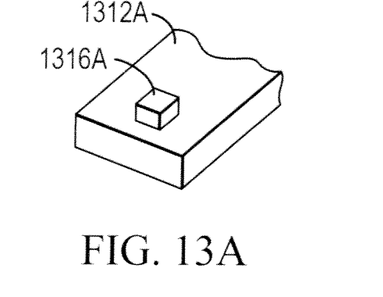
FIG. 13A is a perspective view of a square protrusion in accordance with an exemplary embodiment of the present disclosure.
Figure 13B:
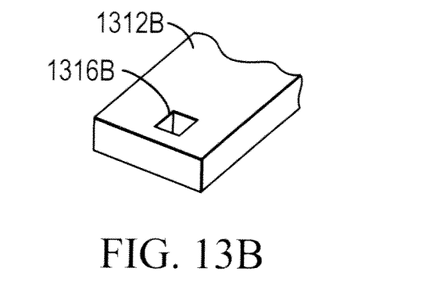
FIG. 13B is a perspective view of a pyramidal protrusion in accordance with another exemplary embodiment of the present disclosure.
Figure 13C:
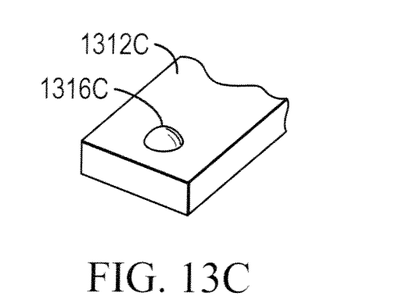
FIG. 13C is a perspective view of a semi-spherical protrusion in accordance with another exemplary embodiment of the present disclosure.
Figure 13D:
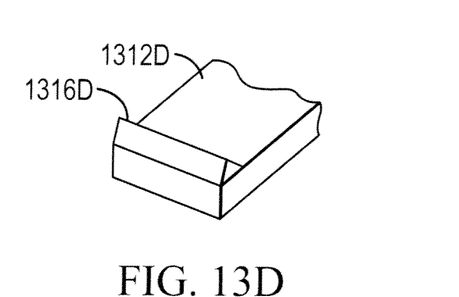
FIG. 13D is a perspective view of a triangular protrusion in accordance with another exemplary embodiment of the present disclosure.
Figure 13E:
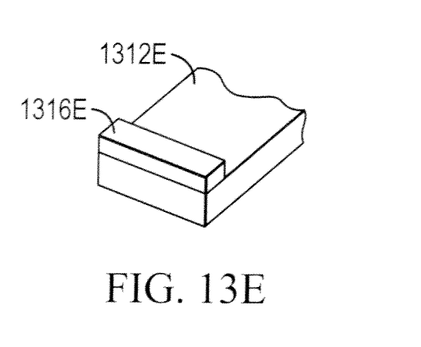
FIG. 13E is a perspective view of a rectangular protrusion in accordance with another exemplary embodiment of the present disclosure.
Figure 13F:
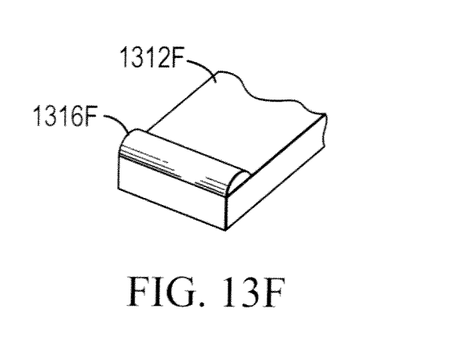
FIG. 13F is a perspective view of a semi-cylindrical protrusion in accordance with another exemplary embodiment of the present disclosure.

Other protrusion configurations are also contemplated by the present disclosure. Various exemplary configurations are shown in FIGS. 13A-13F. In FIG. 13A, a square protrusion 1316a is positioned substantially centrally on deflection portion 1312a. FIG. 13B shows a pyramidal protrusion 1316b on deflection portion 1312b. A centered semi-spherical protrusion 1316c is shown on deflection portion 1312c in FIG. 13C. A triangular, or wedge-shaped, protrusion 1316d extends the entire width of deflection portion 1312d in FIG. 13D. FIG. 13E shows a rectangular protrusion 1316e on deflection portion 1312e that extends the entire width of the deflection portion, as discussed above with reference to the alternative embodiment to FIGS. 6 and 7. In FIG. 13F, a semi-cylindrical protrusion 1316f is shown on deflection portion 1312f.

The protrusions shown in FIGS. 13A-13F are non-limiting examples of various protrusions that may be used according to the present disclosure. One of ordinary skill in the art would recognize that other protrusion shapes, sizes, and/or positions are encompassed by the present disclosure. The selection of the protrusion shapes, sizes, and/or positions may be chosen based on several criteria, such as the implant used, the properties of the material used in either the transfer coping or the implant, the size of the coronal opening of the implant, the size and/or shape of the groove or undercut in the implant, as well as other criteria.

FIGS. 11 and 12 show partial cross-sections taken in a plane of a longitudinal axis of transfer copings engaged with the dental implant 500 according to exemplary embodiments of the present disclosure. In FIG. 11, transfer coping 100, as shown in detail in FIGS. 1-4, comprises support portions 118 and protrusions 116 (e.g., localized protrusions) on deflection portions 112, which are flanked by deflection grooves 114. The protrusions 116 matingly engage an indented region 516' on dental implant 500. In this embodiment, protrusions 116 have a substantially complimentary shape to indented region 516' to increase the area of contact between the transfer coping 100 and the dental implant 500. Friction fit taper 120 fittingly mates to a shoulder 525 of the coronal portion 520' of the dental implant 500. As mentioned above, in an exemplary embodiment, the transfer coping 100 may not comprise the friction fit taper 120, i.e., the angle of the friction fit taper is 0°.

In FIG. 12, transfer coping 700, as shown in the embodiment of FIGS. 7 and 8, comprises support portions 718 and localized protrusions 716 on deflection portions 712, which are flanked by deflection grooves 714. Localized protrusions 716 engage indented region 516' on dental implant 500 in an interference fit, i.e., at least one point of contact exists between the protrusions and the indentation to create a fitting that depends on the deflective properties of the deflection portions of the transfer coping and the friction between the transfer coping and the dental implant. Friction fit taper 720 fittingly mates to coronal portion 520' of the dental implant 500.

As described herein, the various configurations of the implant mating portion, including protrusions, may permit the transfer coping to be used without having to screw the transfer coping to the implant. The combination of support portions and deflection portions may allow the transfer coping to be accurately and securely engaged to the implant without the need to rotate the transfer coping.

Although various exemplary embodiments of transfer copings described herein have been described as configured to be used with dental implants, it is envisioned that the transfer copings in accordance with the present teachings may be configured for use with other types of implants, including, for example, extra-oral and/or orthopedic implants, for which it may be desirable to take an impression. Examples of extra-oral implants include implants used for prosthetic eyes or ears.

The transfer copings according to the present disclosure may comprise any shape or form useful for the intended application. The figures provided show various exemplary geometries and configurations. However, one skilled in the art would understand that transfer copings having different implant mating portions to fit various implants are also contemplated by the present disclosure. For example, one or more protrusions may be provided and configured to engage, such as by snap-fitting, with one or more indentations on a dental implant, and the exemplary embodiments showing two such protrusions and cooperating indentations are non-limiting. Furthermore, other mechanical bonding aids, such as grooves, surface roughening, including friction fitting, or bumps, may be used on the transfer coping in either the implant mating portion or the impression material contact portion. In addition, the transfer coping may comprise other structural features. For example, the coping may comprise protrusions, ridges, or bumps on the surface of the transfer coping to aid in the binding of the transfer coping to the impression material. Such deviations from the structures shown in the figures are contemplated by the present disclosure, and one skilled in the art would readily appreciate that such structural modifications are covered by the present disclosure.

It is noted that, as used in this specification and the appended claims, the singular forms "a," "an," and "the," include plural referents unless expressly and unequivocally limited to one referent. Thus, for example, reference to "a protrusion" can refer to one, two, or more protrusions. As used herein, the term "include" and its grammatical variants are intended to be non-limiting, such that recitation of items in a list is not to the exclusion of other like items that can be substituted or added to the listed items.

It will be apparent to those skilled in the art that various modifications and variation can be made to the transfer copings and methods of the present disclosure without departing from the scope its teachings. Other embodiments of the disclosure will be apparent to those skilled in the art from consideration of the specification and practice of the teachings disclosed herein. It is intended that the embodiments described in the specification be considered as exemplary only.

What is claimed is:

1. A transfer coping configured to take an impression of an implant, the transfer coping comprising:
   an impression material contact portion; and
   an implant mating portion configured to be received within an opening on a coronal portion of an implant, the implant mating portion comprising one or more substantially rigid support portions and one or more deflection portions, wherein the one or more support portions and the one or more deflection portions are separated from one another by axially extending grooves disposed therebetween, wherein an axially extending edge of one of the support portions and an axially extending edge of a circumferentially adjacent one of the deflection portions define one of the grooves, and wherein one or more protrusions are disposed on the one or more deflection portions and are configured to engage in a snap-fit manner with a coordinating feature of an implant to maintain engagement of the transfer coping with the implant to take an impression.

2. The transfer coping of claim 1, wherein the grooves are configured to permit elastic deflection of the one or more deflection portions relative to the one or more substantially rigid support portions.

3. The transfer coping of claim 1, wherein the one or more substantially rigid support portions comprise a plurality of substantially rigid support portions and the one or more deflection portions comprise a plurality of deflection portions.

4. The transfer coping of claim 3, wherein, in a transverse cross-section perpendicular to an axis of the implant mating portion, the implant mating portion comprises a polygonal shape comprising sides defined by the plurality of substantially rigid support portions and the plurality of deflection portions.

5. The transfer coping of claim 4, wherein the deflection portions define opposite sides of the polygonal shape.

6. The transfer coping of claim 3, wherein the one or more protrusions comprise a plurality of protrusions, at least one of the plurality of protrusions being disposed on each of the plurality of deflection portions, respectively.

7. The transfer coping of claim 1, wherein the one or more protrusions has a geometry chosen from spherical, triangular, square, rectangular, pyramidal, annular, and wedge-shaped.

8. The transfer coping of claim 1, further comprising one or more tapered portions configured to engage in a friction fit manner with a tapered portion on the implant, the one or more tapered portions being disposed in an axial direction of the implant mating portion between the impression material contact portion and the rigid support portions.

9. The transfer coping of claim 1, wherein the transfer coping comprises a material chosen from metal, ceramic, plastic, and combinations thereof.

10. The transfer coping of claim 9, wherein the material is radiopaque.

11. The transfer coping of claim 1, wherein the impression material contact portion comprises one or more flanges.

12. The transfer coping of claim 1, wherein the snap-fit engagement is sufficiently strong to permit taking an impression of the transfer coping without using a screw to engage the transfer coping to the implant.

13. The transfer coping of claim 1, wherein each groove comprises a gap or an opening between one of the substantially rigid support portions and one of the deflection portions.

14. The transfer coping of claim 1, wherein each groove extends along and between a length of a respective one of the one or more substantially rigid support portions and a respective one of the one or more deflection portions.

15. A method for taking an impression of an implant, the method comprising:

inserting an implant mating portion of a transfer coping within an opening of the implant, the implant mating portion comprising one or more substantially rigid support portions and one or more deflection portions, wherein the one or more support portions and the one or more deflection portions are separated from one another by axially extending deflection grooves disposed therebetween, wherein an axially extending edge of one of the rigid support portions and an axially extending edge of a circumferentially adjacent one of the deflection portions define one of the grooves;

engaging the transfer coping to the implant by snap-fitting one or more protrusions on the one or more deflection portions with a respective coordinating feature on the implant, wherein the snap-fitting engagement is sufficiently strong to maintain engagement of the transfer coping with the implant to take an impression; and forming an impression around the impression material contact portion with an impression material.

16. The method of claim 15, further comprising removing the impression with the transfer coping attached.

17. The method of claim 16, wherein removing the impression with the transfer coping attached comprises applying a force of about 0.5 pounds to about 6 pounds.

18. The method of claim 16, wherein removing the impression with the transfer coping attached comprises removing the impression without first loosening a screw engaging the transfer coping and the implant.

19. The method of claim 15, wherein engaging the transfer coping comprises elastically deflecting the one or more deflection portions relative to the one or more substantially rigid support portions, and returning the deflection portion to a non-deflected position.

20. The method of claim 19, wherein engaging the transfer coping further comprises friction fitting a tapered portion of the transfer coping with a coronal portion of the implant, the tapered portion being disposed in an axial direction of the implant mating portion between the impression material contact portion and the rigid support portions.

21. The method of claim 15, wherein forming the impression comprises forming the impression without a screw engaging the transfer coping to the implant.

22. The method of claim 15, wherein inserting the implant mating portion comprises inserting the implant mating portion of the transfer coping within an opening of a dental implant, an extra-oral implant, or an orthopedic implant.

23. A transfer coping configured to take an impression of an implant, the transfer coping comprising:

an impression material contact portion; and an implant mating portion configured to be received within an opening on a coronal portion of an implant, the implant mating portion comprising one or more substantially rigid support portions and one or more deflection portions, wherein the one or more support portions and the one or more deflection portions are separated from one another by grooves disposed therebetween, wherein the grooves are parallel to one another, and wherein one or more protrusions are disposed on the one or more deflection portions and are configured to engage in a snap-fit manner with a coordinating feature of an implant to maintain engagement of the transfer coping with the implant to take an impression.

24. A transfer coping configured to take an impression of an implant, the transfer coping comprising:

an impression material contact portion; and an implant mating portion configured to be received within an opening on a coronal portion of an implant, the implant mating portion comprising at least one substantially rigid support portion and at least one deflection portion, wherein in a transverse cross-section perpendicular to a longitudinal axis of the implant mating portion, the at least one substantially rigid support portion and the at least one deflection portion are arranged around a circumference of the implant mating portion and are separated from one another by grooves disposed therebetween, the grooves extending at least partially along a height of the at least one rigid support portion along said axis and terminating at a free end of the at least one rigid support portion, and wherein at least one protrusion is disposed on the at least one deflection portion and is configured to engage in a snap-fit manner with a coordinating feature of an implant to maintain engagement of the transfer coping with the implant to take an impression.

25. The transfer coping of claim 24, wherein the grooves are sized and shaped to permit the one or more deflection portions to deflect radially inwardly and radially outwardly relative to the remainder of the implant mating portion.

26. The transfer coping of claim 24, wherein the at least one substantially rigid support portion comprises a plurality of substantially rigid support portions and the at least one deflection portion comprises a plurality of deflection portions.

27. The transfer coping of claim 26, wherein the implant mating portion comprises a polygonal shape comprising sides defined by the plurality of substantially rigid support portions and the plurality of deflection portions.

28. The transfer coping of claim 27, wherein the deflection portions define opposite sides of the polygonal shape.

29. The transfer coping of claim 26, wherein the at least one protrusion comprises a plurality of protrusions, each of the plurality of protrusions being disposed on a respective one of the plurality of deflection portions.

30. The transfer coping of claim 24, wherein the at least one protrusion has a geometry chosen from spherical, triangular, square, rectangular, pyramidal, annular, and wedge-shaped.

31. The transfer coping of claim 24, further comprising one or more tapered portions configured to engage in a friction fit manner with a tapered portion on the implant.

\* \* \* \* \*